United States Patent
Bijjani et al.

(10) Patent No.: US 7,023,957 B2
(45) Date of Patent: Apr. 4, 2006

(54) METHOD AND APPARATUS FOR TRANSMITTING INFORMATION ABOUT A TARGET OBJECT BETWEEN A PRESCANNER AND A CT SCANNER

(75) Inventors: Richard R. Bijjani, Westford, MA (US); Richard F. Eilbert, Lincoln, MA (US); Shunghe Shi, Southboro, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

(21) Appl. No.: 10/717,051

(22) Filed: Nov. 19, 2003

(65) Prior Publication Data

US 2005/0053184 A1  Mar. 10, 2005

Related U.S. Application Data

(63) Continuation of application No. 10/068,459, filed on Feb. 6, 2002, now Pat. No. 6,816,571.

(51) Int. Cl.
*G01N 12/087* (2006.01)

(52) U.S. Cl. .................. 378/57; 378/5; 378/7; 378/98.9

(58) Field of Classification Search .................... 378/5, 378/7, 57, 86, 87, 89, 90, 98.9, 98.8
See application file for complete search history.

(56) References Cited

U.S. PATENT DOCUMENTS

| | | | |
|---|---|---|---|
| 4,020,346 A | 4/1977 | Dennis | |
| 4,064,440 A | 12/1977 | Roder | |
| 4,217,641 A | 8/1980 | Naparstek | |
| 4,247,774 A | 1/1981 | Brooks | |
| 4,539,648 A | 9/1985 | Schatzki | |
| 4,580,219 A | 4/1986 | Pelc et al. | |
| 4,590,558 A | 5/1986 | Glover et al. | |
| 4,709,333 A | 11/1987 | Crawford | |
| 4,759,047 A | 7/1988 | Donges et al. | |
| 4,788,704 A | 11/1988 | Donges et al. | |
| 4,941,162 A | 7/1990 | Vartsky et al. | |
| 4,957,250 A | 9/1990 | Hararat-Tehrani | |
| 5,070,519 A | 12/1991 | Stein et al. | |
| 5,109,691 A | 5/1992 | Corrigan et al. | |
| 5,125,015 A | 6/1992 | Shimoni et al. | |

(Continued)

OTHER PUBLICATIONS

Roder, Fredrick L., "Explosives Detection By Dual-Energy Computed Tomography," Proc. SPIE, Apr. 19-20, 1979, pp. 171-178.

(Continued)

*Primary Examiner*—Allen C. Ho
(74) *Attorney, Agent, or Firm*—Wolf, Greenfield, & Sacks, P.C.

(57) ABSTRACT

A method or apparatus for analyzing an object includes an X-ray prescanner that performs a prescan of the object to determine prescan information about the object. Then, a CT scanner performs a CT scan on at least one plane of the object based on the prescan information to determine CT information. In one embodiment, if the CT scan of the object includes or is in the vicinity of metal, then metal artifact correction of a reconstructed image from the CT scan is performed based on the prescan information. In another embodiment, a processor analyzes the CT information and the prescan information to determine whether to update the prescan information based on the CT information

12 Claims, 5 Drawing Sheets

U.S. PATENT DOCUMENTS

| | | | |
|---|---|---|---|
| 5,162,652 A | 11/1992 | Cohen et al. | |
| 5,182,764 A | 1/1993 | Peschmann et al. | |
| 5,243,664 A * | 9/1993 | Tuy | 382/130 |
| 5,319,547 A | 6/1994 | Krug et al. | |
| 5,323,004 A | 6/1994 | Ettinger et al. | |
| 5,367,552 A * | 11/1994 | Peschmann | 378/57 |
| 5,490,218 A | 2/1996 | Krug et al. | |
| 5,600,303 A | 2/1997 | Husseiny et al. | |
| 5,600,700 A | 2/1997 | Krug et al. | |
| 5,642,393 A | 6/1997 | Krug et al. | |
| 5,661,774 A | 8/1997 | Gorden et al. | |
| 5,666,391 A | 9/1997 | Ohnesorge et al. | |
| 5,805,660 A | 9/1998 | Perion et al. | |
| 5,838,758 A * | 11/1998 | Krug et al. | 378/53 |
| 5,905,809 A * | 5/1999 | Timmer | 382/131 |
| 5,933,471 A | 8/1999 | Kalvin | |
| 5,953,444 A | 9/1999 | Joseph et al. | |
| 6,018,562 A | 1/2000 | Willson | |
| 6,026,143 A | 2/2000 | Simanovsky et al. | |
| 6,076,400 A | 6/2000 | Bechwati et al. | |
| 6,088,423 A | 7/2000 | Krug et al. | |
| 6,094,467 A * | 7/2000 | Gayer et al. | 378/4 |
| 6,094,472 A | 7/2000 | Smith | |
| 6,118,850 A | 9/2000 | Mayo et al. | |
| 6,125,193 A | 9/2000 | Han | |
| 6,163,591 A | 12/2000 | Benjamin | |
| 6,198,795 B1 | 3/2001 | Naumann et al. | |
| 6,218,943 B1 | 4/2001 | Ellenbogen | |
| 6,256,404 B1 | 7/2001 | Gordon et al. | |
| 6,272,230 B1 | 8/2001 | Hiraoglu et al. | |
| 6,345,113 B1 | 2/2002 | Crawford et al. | |
| 6,359,961 B1 | 3/2002 | Aufrichtig et al. | |
| 6,600,801 B1 | 7/2003 | Raupach | |
| 6,707,879 B1 * | 3/2004 | McClelland et al. | 378/57 |
| 2002/0172324 A1 | 11/2002 | Ellenbogen et al. | |
| 2002/0176531 A1 | 11/2002 | McClelland et al. | |
| 2002/0186862 A1 | 12/2002 | McClelland et al. | |
| 2003/0085163 A1 | 5/2003 | Chan et al. | |
| 2004/0076262 A1* | 4/2004 | Shao et al. | 378/196 |
| 2004/0120456 A1 | 6/2004 | Ellenbogen et al. | |
| 2005/0008119 A1 | 1/2005 | McClelland et al. | |
| 2005/0031076 A1 | 2/2005 | McClelland et al. | |
| 2005/0111619 A1 | 5/2005 | Bijjani et al. | |

OTHER PUBLICATIONS

Office of Technology Assessment, Congressional Board of the 102d Congress, publicly released Feb. 26, 1991, entitled "Technology Against Terrorism, The Federal Effort".

I. D. Jupp et al, "The Non-Invasive Inspection of Baggage Using Coherent X-ray Scattering," IEEE Transactions on Nuclear Science, vol. 47, No. 6, Dec. 2000, pp. 1987-1994.

Michael J. Barrientos, "Screener Threat Detection Performance With Three Dimensional X-ray Imaging," International Carnahan Conference on Security Technology, 2000, Proc. IEEE 34th Annual 2000, pp. 178-191.

S.P. Beevor et al., "Non-Invasive Inspection Of Baggage Using Coherent X-ray Scattering," European Convention On Security and Detection, 1995.

* cited by examiner

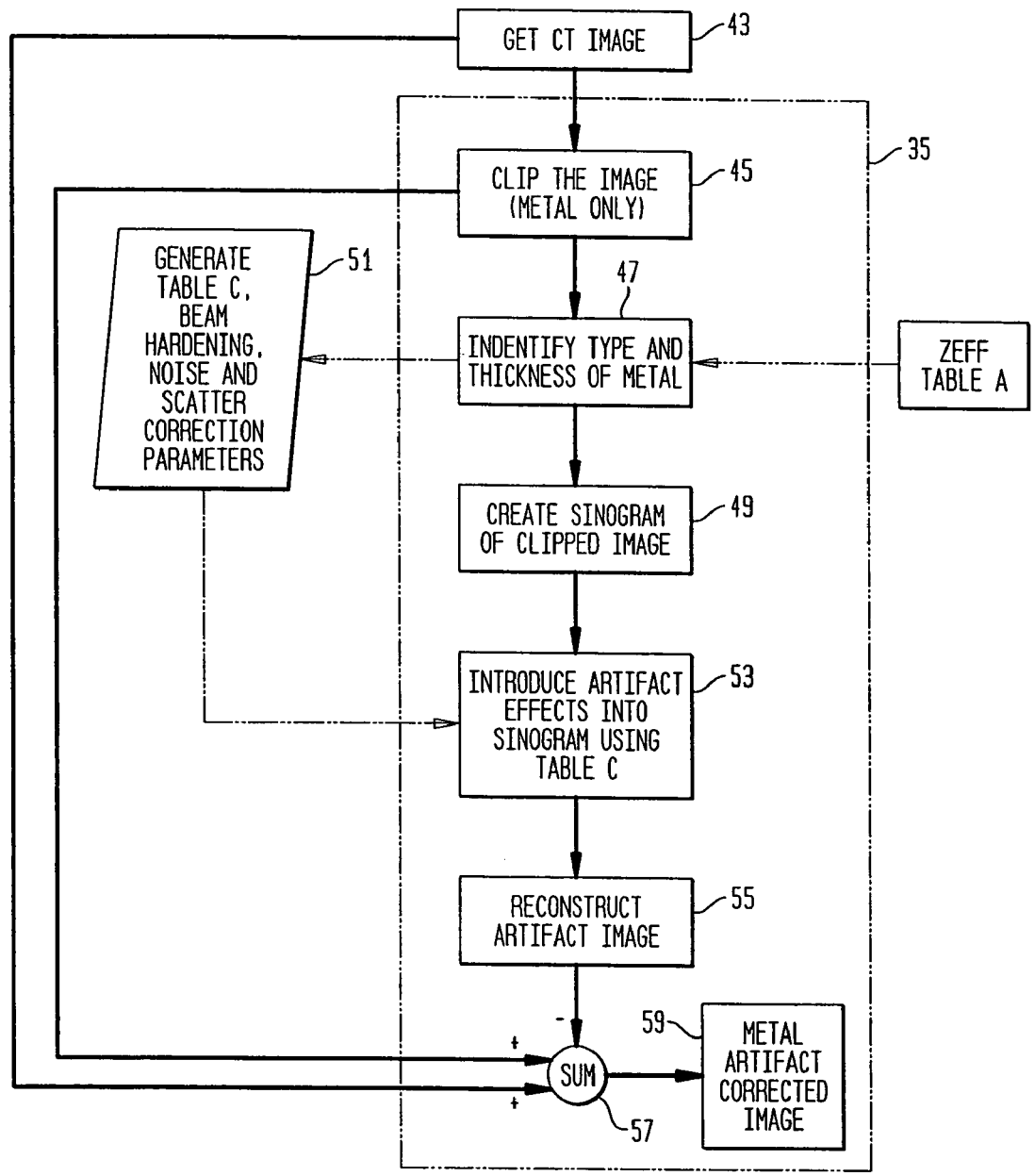

METHOD AND APPARATUS FOR TRANSMITTING INFORMATION ABOUT A TARGET OBJECT BETWEEN A PRESCANNER AND A CT SCANNER

CROSS REFERENCES TO RELATED APPLICATIONS

This application is a continuation of application Ser. No. 10/068,459, filed on Feb. 6, 2002, now U.S. Pat. No. 6,816,571, entitled "Method and Apparatus For Transmitting Information About A Target Object Between A Prescanner and A CT Scanner."

FIELD OF THE INVENTION

The present invention is directed to the field of X-ray detection systems.

BACKGROUND OF THE INVENTION

There exists a need for improved systems and methods of screening baggage for explosives, weapons, and other contraband. Some existing systems employ X-ray scanners, computed tomography (CT) scanners, or other imaging devices to detect concealed objects. In some such systems, a CT scanner is preceded by an X-ray scanner, which performs a "prescanning" function to determine initial information on the contents of an article of baggage. Existing X-ray based systems provide differing degrees of sophistication in terms of their ability to analyze baggage based on the X-ray data obtained. Some, for example, balance the speed of the baggage screening with the accuracy and reliability with which contraband is detected. While the prescanning function discussed above may increase the accuracy and reliability with which contraband is detected, there exists a need for improved systems and methods of screening baggage.

SUMMARY OF THE INVENTION

One embodiment of the invention is directed to a method or apparatus for analyzing an object in which a dual energy X-ray prescanner performs a prescan of the object to determine prescan information about the object. Then, a CT scanner performs a CT scan on at least one plane of the object based on the prescan information. If the CT scan of the object includes or is in the vicinity of metal, then metal artifact correction of a reconstructed image from the CT scan may be performed using the prescan and CT scan information.

Another embodiment of the invention is directed to a method or apparatus for analyzing an object in which a prescanner, which need not be a dual energy prescanner, performs a prescan of the object to determine prescan information. Then, a CT scanner performs a CT scan of the object to determine CT information. A processor analyzes the CT information and the prescan information to determine whether to update the prescan information based on the CT information.

While the description and claims herein recite use of a CT scanner, such term is intended to cover any device that measures at least density of an object scanned by the device.

BRIEF DESCRIPTION OF THE DRAWINGS

FIG. 7 is a flow diagram illustrating a method for obtaining a CT image and predicting and correcting metal artifacts of the CT image according to one embodiment of the invention.

DETAILED DESCRIPTION

The present invention relates to a system or method in which a prescanner X-ray device and a downstream (of the prescanner) computed tomography (CT) device scan an object. The object may be located within a piece of baggage, a manufactured product, the human body, or some other item penetrable by X-rays. Information collected on the object may be transmitted from the prescanner to the CT scanner and/or from the CT scanner to the prescanner.

Figure 1:
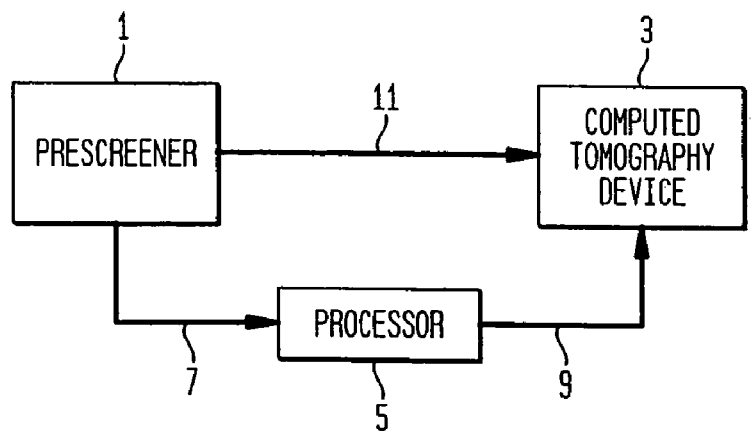
FIG. 1 is a block diagram of an apparatus for transmitting information from a prescanner device to a CT scanner device according to one embodiment of the invention.

One embodiment of the present invention, illustrated in FIG. 1, is directed to a method and apparatus for transmitting information from a prescanner device 1 to a downstream CT scanner device 3. This can be accomplished in any of numerous ways, and the present invention is not limited to any particular one of such ways.

In accordance with one illustrative embodiment, information from prescanner device 1 is transmitted from prescanner device 1 to a processor 5 via a data link 7. Data link 7, and any other data link described herein, is not limited to any particular type of link and may be implemented using any suitable means for transmitting information, such as an Ethernet link.

Processor 5 may process the information transmitted from the prescanner device, and transmit the processed information, or a control signal with instructions based on the processed information, to CT scanner device 3 via a data link 9. Processor 5 may be located external or internal to CT scanner device.

It should be appreciated that while FIG. 1 illustrates both a direct communication link, such as data link 11, and an indirect communication link via a processor, such as data links 7 and 9, both communications links are not required. One such communication link, or any other communication link that may be envisioned by one skilled in the art, may be implemented.

Prescanner device 1 may be any of numerous multiple energy X-ray devices. For example, prescanner device 1 may be a single or multi-view dual energy line scanning X-ray device, a dual energy CT scanner device, or any other device capable of measuring effective atomic number characteristics of an object, the significance of which will be appreciated from the forthcoming discussion. U.S. Pat. No.

5,838,758 (Krug), which is hereby incorporated by reference, teaches dual energy X-ray inspection systems, any of which may be employed as the prescanner device according to an embodiment of the invention.

CT scanner device 3 may be any of numerous devices for performing computed tomography or, more generally, may be any device capable of measuring density characteristics of an object. Prescanner device 1 and CT scanner device 3 may be implemented as separate units, as shown in FIG. 1, or as a single unit having both prescanning and CT scanning functionalities.

The screening systems described herein may be used in a variety of applications to recognize and detect target objects of interest. Target objects may include, but are not limited to, concealed objects (e.g., explosive devices or other weapons) inside a container (e.g., baggage), defects (e.g., cracks, air bubbles, or impurities) in articles of manufacture (e.g., commercial products), and areas of interest (e.g., tumors or other masses, including masses located near bone, metal, or another high-density material from which artifacts may result) within the body. Thus, the invention described herein may be used, for example, in settings such as airports, manufacturing plants, and hospitals, and other settings in the travel, commercial, and medical industries.

Certain characteristics of target objects discussed above can be determined mathematically based on the absorption of X-ray radiation by the object. The absorption of X-ray radiation by a material in an item is proportional to the degree of X-ray attenuation and is dependent on the energy of the X-ray radiation and the following material parameters: thickness, density, and atomic number. The relationship between these values can be described by Equation 1:

$$I_x = I_0 \exp[-(\mu/\rho)x] \quad (1)$$

where, $I_x$ is the intensity of the X-ray radiation after passing through a material, $I_0$ is the intensity of the X-ray radiation before passing through a material, $\mu/\rho$ is the mass attenuation coefficient; and x is obtained by multiplying the thickness of the material by its density. It should be appreciated that since X-ray absorption by a material is dependent on the thickness, density, and atomic number of the material, absorption and attenuation may be most accurately determined when all three parameters of a material are known. The scanning devices described herein can accurately determine the thickness, density, and/or atomic number of an object, and these parameters may be used to determine whether an object is a target object.

In the embodiment of FIG. 1, prescanner device 1 performs an initial scan of an item, and CT scanner device 3 then may perform a subsequent scan of one or more areas of interest within the item, which are determined based on the initial scan. Prescanner device 1 may "feedforward" information relating to possible target object areas determined during the initial prescan to the CT scanner device 3 so that CT scanner device 3 scans only those slices that are located in regions where target objects may exist.

This method reduces the number of slices necessary to be taken by the CT scanner, including the number of slices taken through metal, to detect a target object and increases the accuracy with which target objects are detected. A CT scanner device employed alone to scan an item performs CT scans of planes (or "slices") of the item and provides information on the three dimensional spatial configurations of objects therein. While this technique is useful in identifying target objects within the scanned item, each CT scan is time consuming and has a limited image quality. Numerous of these time-consuming scans are required to ensure no target area is missed. By employing prescanner device 1 upstream of the CT scanner, according to one embodiment of the present invention, possible target objects and their two-dimensional locations are determined in a quick (relative to a CT scan) prescan. A significant advantage lies in reducing the number of slices, and thereby reducing the scan time, for an item.

In addition to reducing the scan time of the CT scanner device, the feeding forward of information from prescanner device 1 to CT scanner device 3 may increase the accuracy of the CT scan images. For example, as will be described in greater detail below, for those slices that are in the vicinity of metal, the fedforward information can be used to perform metal artifact correction, thereby increasing the accuracy of any reconstructed image from the CT scan and ability to detect target objects.

Figure 2:
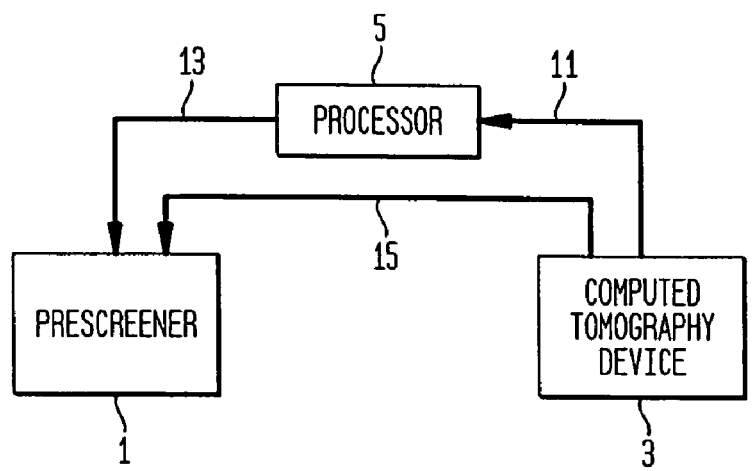
FIG. 2 is a block diagram of an apparatus for transmitting information from a CT scanner device to a prescanner device according to one embodiment of the invention.

Another embodiment of the present invention, illustrated in FIG. 2, is directed to a method or apparatus for transmitting information from CT scanner device 3 to prescanner device 1. According to this embodiment, information relating to a potential target object scanned by CT scanner device 3 is transmitted ("fedback") to a processor to determine whether to update information collected by prescanner device 1 relating to the potential target object. For example, information collected by the prescanner device, relating to the effective atomic number and mass of a potential target object, may be inaccurate for areas of the scan where the potential target object overlaps with another object or objects. A CT scan of a region including the potential target object, by obtaining density information through scans of slices in different orientations, can distinguish the potential target object from background objects, and thereby determine the precise boundaries of the target object. This fedback information is analyzed by the processor to determine whether to update and improve the accuracy of the information (e.g., effective atomic number and mass) collected by prescanner device 1.

According to one embodiment of the invention (FIG. 2), the processor is located internal to prescanner device 1, and information from CT scanner device 3 is transmitted to the processor in prescanner device 1. The information may be transmitted in any of numerous ways, and the present invention is not limited to any particular one of such ways. For example, information from CT scanner device 3 may be transmitted from CT scanner device 3 to a processor 5 via data link 11. Processor 5 may process the information transmitted from CT scanner device 3, and transmit the processed information to prescanner device 1 via a data link 13. Alternatively, information may be transmitted directly from CT scanner device 3 to prescanner device 1 via a data link 15. According to another embodiment of the invention, the information from CT scanner device 3 is not transmitted to prescanner device 1, but rather is transmitted to a processor located external to prescanner device 1. For example, information may be transmitted to a processor located in CT scanner device 3 or to a processor in an external computing system.

Figure 3:
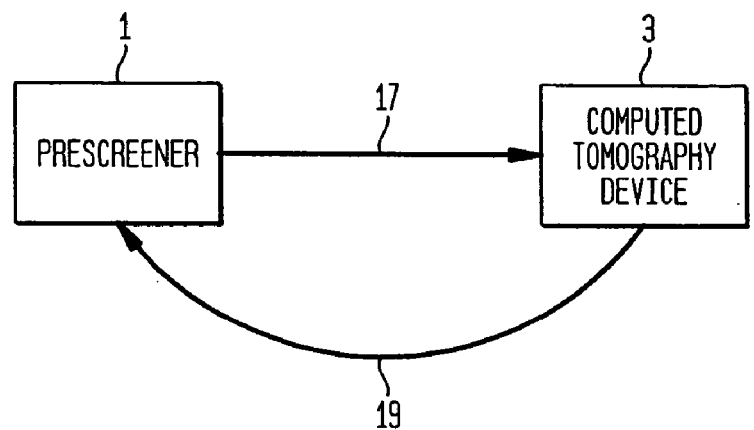
FIG. 3 is a block diagram of an apparatus for transmitting information between a CT scanner device and a prescanner device according to one embodiment of the invention.

Another embodiment of the present invention, illustrated in FIG. 3, is directed to transmitting information from prescanner device 1 to CT scanner device 3, referred to as the "feedforward mode", and from CT scanner device 3 to prescanner device 1, referred to as the "feedbackwards mode." This embodiment combines the embodiments of FIGS. 1 and 2, above. As discussed previously, in the feedforward mode, information relating to a two-dimensional location of a potential target object is transferred from prescanner device 1 to CT scanner device 3 (or a processor coupled to CT scanner 3) to determine locations for CT slices to be performed, thereby reducing the CT scan time. Further in the feedforward mode, information relating to the effective atomic number and mass of potential target objects is transferred from prescanner device 1 to CT scanner device 3 (or a processor coupled to CT scanner 3) to increase the accuracy of the CT images, particularly for those slices that are in the vicinity of metal. In the feedback mode, density information collected by CT scanner device 3 is transmitted to prescanner 1 (or a processor coupled to prescanner 1) to enable the prescanner to update and improve the accuracy of the effective atomic number and mass information collected by prescanner device 1.

In the embodiment of FIG. 3, information from prescanner device 1 is transmitted to CT scanner device 3 via data link 17, and information from CT scanner device 3 is transmitted to prescanner device 1 via a data link 19. Data link 17 and data link 19 may be separate data paths or may be implemented as a single data path, such that information is transmitted for both of the data links via a single medium. Further, data link 17 and data link 19 may be direct links or may pass through another device, such as a processor. Data processing may occur in an external processor, or may occur internal to each of prescanner device 1 and CT scanner device 3. As discussed above, though prescanner device 1 and CT scanner device 3 are illustrated separately in FIG. 3, it is not necessary that each be implemented as a separate unit. Rather, prescanner device 1 and CT scanner device 3 may be implemented as a single unit having both prescanning and CT scanning functionalities.

Figure 4:
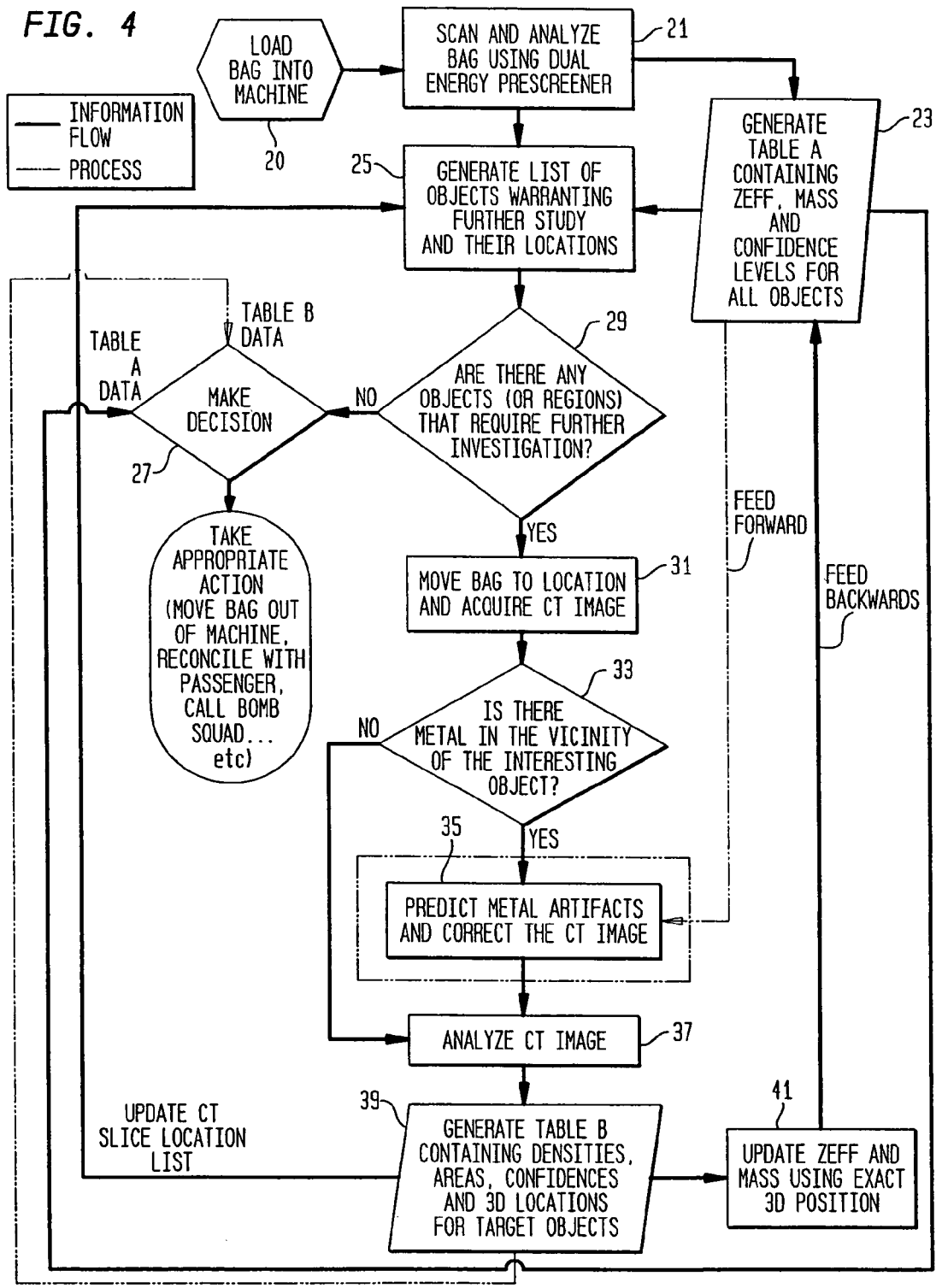
FIG. 4 is a flow diagram illustrating a method for transmitting information between a CT scanner device and a prescanner device according to one embodiment of the invention.

FIG. 4 is a flow diagram according to one embodiment in which information may be transmitted from prescanner device 1 to CT scanner device 3 in the feedforward mode, and from CT scanner device 3 to prescanner device 1 in the feedbackwards mode. It should be appreciated that, as discussed above, the feedforward and feedbackwards modes need not be implemented in the same screening system and that each may be implemented independently in a separate system. The flow diagram of FIG. 4 shows both information (i.e., data) flow (in phantom lines) and process flow (in solid lines).

Beginning with step 20, an item (e.g., an article of baggage) to be screened is loaded into a machine of the invention. In step 21, the item is scanned and analyzed using the prescanner device 1. The prescanner device 1 may be a line scanner, such as one of the VIS series offered by PerkinElmer Detection Systems, the assignee herein. The item is initially loaded into the prescanner device 1 for scanning. For example, a human operator may place the item on a conveyor which, with the aid of a motion controller, moves the item through prescanner device 1. In one embodiment, prescanner device 1 has at least two X-ray sources for generating X-ray beams and may have one or more X-ray detectors for receiving X-ray beams. The X-ray image resulting from the scan consists of a two-dimensional array of pixels representing a view of the three-dimensional item from one angle. A processor, either internal or external to prescanner device 1, calculates the attenuation of the generated X-rays penetrating the item for each pixel. According to one embodiment of the invention, alternate pulses of high energy X-rays (e.g., 150 kV) and low energy X-rays (e.g., 75 kV) are respectively generated by dual X-ray sources, and the processor calculates the attenuation for each pixel of the image resulting from the respective high energy and low energy beams.

In a step 23, a table (Table A) is generated containing atomic number and mass characteristics for each object. Table A may be stored electronically by a memory (not shown) coupled to a processor. Both the processor and the memory may be either internal or external to prescanner device 1. An object may be defined as any region having similar atomic number and mass characteristics. The calculated attenuation of the high energy and low energy beam pulses for each pixel of the scanned item are used to determine the effective atomic number of all objects. To derive the effective atomic number of each object based on the attenuation, the attenuation of X-rays at each different energy level is analyzed. One method for doing so is described in U.S. Pat. No. 5,838,758 (Krug), incorporated by reference herein. It is known that materials with a high effective atomic number (e.g., metals) absorb low energy X-ray radiation more strongly, whereas materials with a low effective atomic number (e.g., organic materials) absorb high energy X-ray radiation more strongly. Thus, the effective atomic number of each object may be determined by analyzing the attenuation of low and high energy X-rays by each pixel. To determine the effective atomic number for a particular object, all pixels within the object are compared to pixels surrounding the object and a histogram is created, where the mode (peak of the histogram) represents the effective atomic number.

In addition to effective atomic number information, Table A may also contain mass information for each object. The mass for each pixel may also be determined based on the X-ray attenuation of both the high and low energy X-rays. The relationship between X-ray attenuation and material mass (i.e., thickness) is logarithmic; X-ray radiation decreases logarithmically as the material thickness increases. Thus, mass may be estimated by analyzing the attenuation of X-rays of all energies by materials within an item. To determine the mass for a particular object, mass values for all pixels within an object are added.

In an embodiment, Table A also contains confidence values for the effective atomic number and mass values for each object. Confidence values for the effective atomic number and mass values represent a probability or range of probabilities that the atomic number and mass data are correct. To determine a confidence level for the effective atomic number value or mass value of a particular object, a feature vector denoting properties such as compactness, connectiveness, gradients, histogram spread and other features may be used.

Numerous known procedures are available for determining the confidence level. One such procedure uses machine vision technology for object classification. Machine vision technology includes: (1) segmenting a group of picture elements from their background, (2) describing that group of picture elements by a set of features, and (3) using the resulting feature vector to classify the picture elements.

One software tool available for such object classification is Image Process and Analysis Software offered by Data Translation, Inc. as SP0550. Other software packages that provide similar tools for algorithm development include: Checkpoint® by Cognex Corporation of Natick, Mass., Framework® by DVT of Woodcliff Lake, N.J., and the Powervision® family of products of RVSI of Canton, Mass. The invention need not be limited to the features found in the exemplary software packages mentioned. There are numerous other approaches as described, for examples, in the following textbooks:

1. Machine Vision: Theory, Algorithms, Practicalities (Signal Processing and its Applications Series), by E. R. Davies;
2. Computer Vision and Image Processing: A Practical Approach Using CVIPTools (BK/CD-ROM), by Scott E. Umbaugh;
3. Algorithms for Image Processing and Computer Vision, by James R. Parker; and
4. Feature Extraction in Computer Vision and Image Processing, by Mark Nixon and Alberto Aguado.

A target object, such as an explosive, has a typical effective atomic number and mass value. Further, for a particular range of atomic number values, a particular range of mass values will be characteristic of a target object. Thus, it is useful to consider both atomic number and mass values in determining whether a target object is present.

Figure 6:
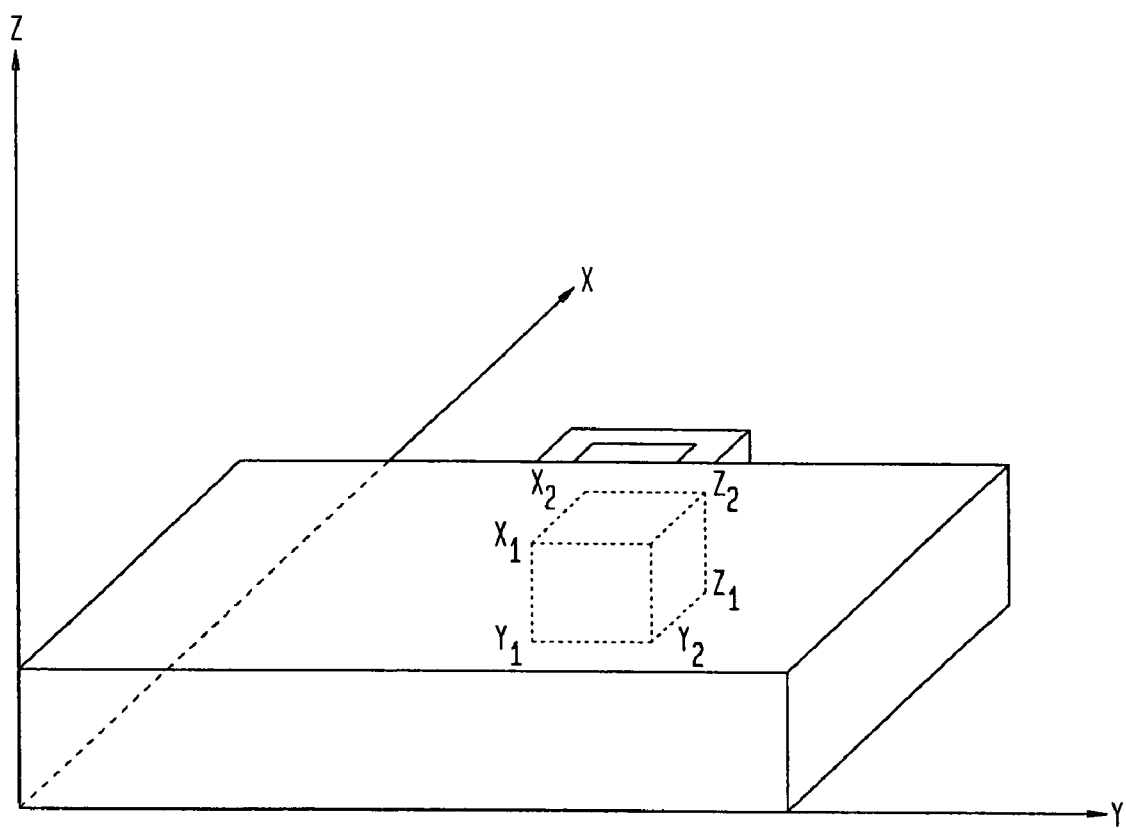
FIG. 6 is a diagram illustrating reference coordinates for a scanned item.

In a step 25, a list of objects warranting further study (i.e., objects of interest), including the locations for the objects, is generated. The atomic number characteristics of Table A can be used to differentiate potential target objects from the background, since different objects will generally have different effective atomic numbers. A potential target object may comprise a collection of pixels in close proximity having atomic number values that fall within a certain range. For example, a weapon or explosive may comprise a collection of pixels having high effective atomic number values that fall within a particular range. Thus, it is possible to determine two-dimensional coordinates (e.g., $x_1$–$x_2$, $z_1$–$z_2$ in FIG. 6) of a potential target object based on effective atomic number and mass information.

While the list of objects warranting further study and two-dimensional coordinates associated with each object may be generated automatically, it is also possible that a human operator may manually determine the information. For example, an operator may view an X-ray image to determine objects of interest and their respective locations in two dimensions. Thus, the prescan analysis may be performed automatically or manually, and the invention is not limited to either method of analysis.

Once a location of an object of interest, or a region thereof, has been determined, a CT scan of the object or region of interest may be performed. Locations of slices (i.e., two-dimensional planes) in the item to be scanned are chosen to coincide with a potential target object. Some target objects, such as explosives, are typically found near metal objects (e.g., wires, batteries). Metal, due in part to its high density, may cause artifacts in an image in the region surrounding the metal. Thus, if a potential target object is located near metal, it is preferable to choose a slice that includes the target object, but that is not in the vicinity of the metal. However, if a slice near metal is chosen, according to one aspect of the invention, a metal artifact correction is performed to correct for the image artifacts, as will be described in step 35.

If, after step 25, there are no objects warranting further study, a decision may be made as to an appropriate course of action, based on the prescan information (FIG. 4, step 27). For example, an operator of an X-ray system in an airport may decide to return the baggage to the passenger, search the baggage by hand, or call the bomb squad. Alternatively, an algorithm may be used to automatically determine an appropriate course of action. If, in step 29, there are objects warranting further study, the item (e.g., baggage) is transferred to the CT scanner device, for example via the conveyor. If there are no objects warranting further study, the item may or may not be transferred to the CT scanner device. According to one aspect of the invention, the item may be transferred to the CT scanner device when no objects warranting further study have been detected so that undetected objects (e.g., sheet explosives) may be screened for.

In step 31, CT images are generated for the item cross-sections identified in step 25, if any. To form a CT image of a cross-section (i.e., slice) of an item, a finely collimated beam of radiation is passed through the item in the desired slice plane, and the attenuation is measured. The process is repeated and a set of projections is acquired as the X-ray beam is passed through the object at different angles. A reconstructed image of the two-dimensional distribution of the linear attenuation coefficient, $\mu(x,y)$, may be obtained from these projections. If the projections could be acquired with an infinitely narrow X-ray beam, and the angular increment at which the X-ray beam is passed was negligible, the result would be a continuous set of projections. Displayed as a two-dimensional function, the continuous set of projections is referred to as the sinogram. An image may be reconstructed from the sinogram by implementing any of a number of well-known reconstruction techniques including, but not limited to, back projection, iteration, Fourier transform, and filtered back projection.

Figure 5:
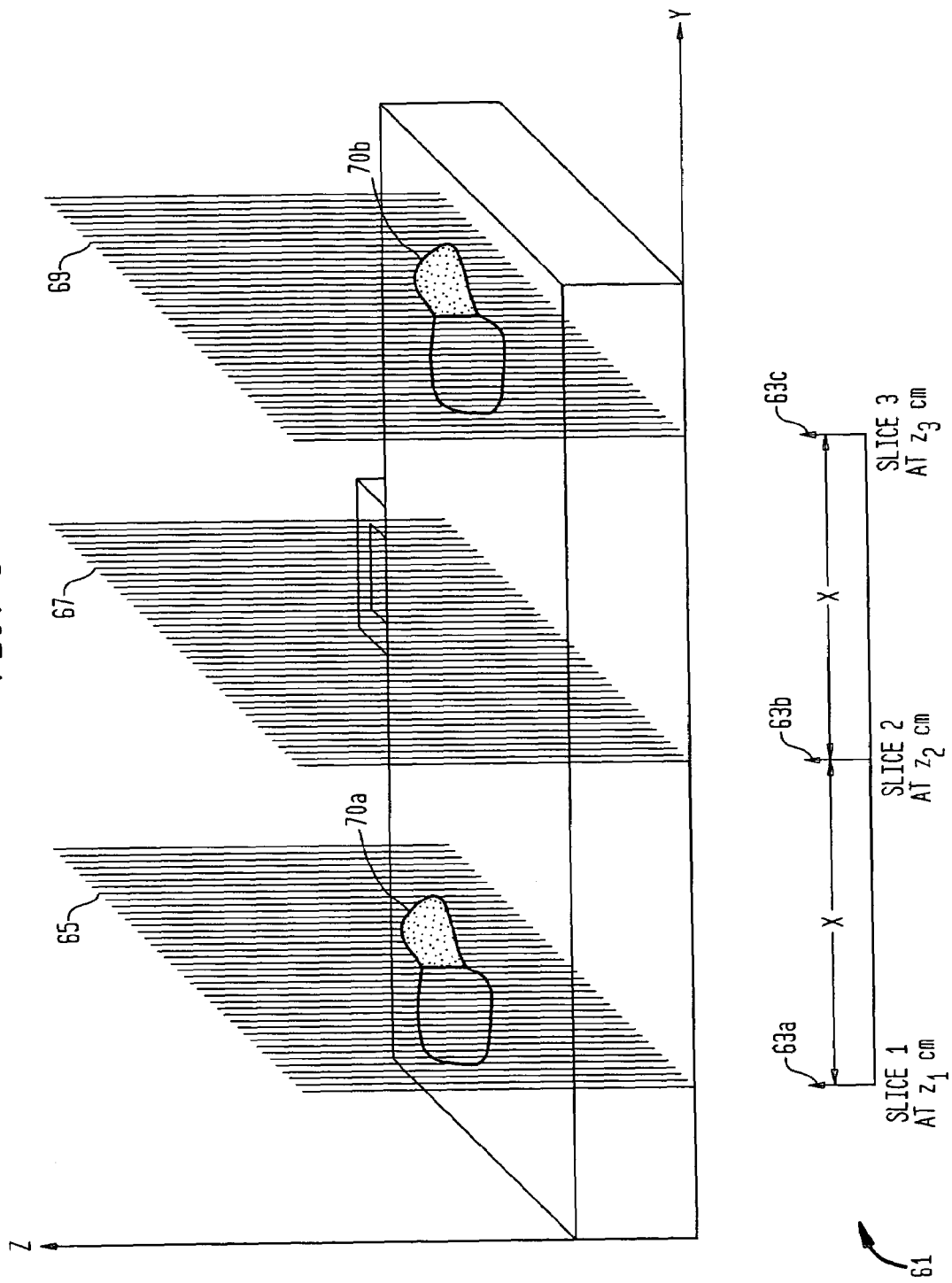
FIG. 5 is a diagram illustrating a grid for performing CT scans at intervals.

As discussed above, a CT image of a slice results in a two-dimensional image of a cross-sectional plane of the scanned item. The image consists of an array of pixels (e.g., 900 pixels×512 pixels). According to one illustrative embodiment shown in FIG. 5, CT scanner device 3 performs scans at locations along a grid 61, such that slices are imaged at predetermined intervals 63*a–c* along the length of the item. For example, an article of baggage may be imaged every distance x along its length. In FIG. 5, a first slice 65 is imaged at $z_1$ cm, a second slice 67 is imaged $z_2$ cm=$(z_1+x)$ cm, and a third slice 69 is imaged at $z_3$ cm=$(z_1+2x)$ cm. Performing scans according to a grid pattern ensures that potential target objects that may not have been identified as warranting further investigation in step 25 are imaged. For example, sheet explosives may evade identification by the prescanner device because they are thin in profile and minimally attenuate X-rays. The CT scanner, on the other hand, may image a number of planes transecting the sheet explosive, and thus may more readily detect the sheet explosive. Preferably, the imaging points on the grid, discussed above, coincide with the objects warranting further study identified in step 25. For example, the first and third slices in FIG. 5 intersect objects 70*a,b*. If not all objects of interest are accommodated by the grid, additional slices may be taken. Further, the grid is preferably positioned to avoid taking slices of metal objects, for the reasons discussed previously.

In step 33, it is determined whether any imaged object of interest is in the vicinity of a metal object. Additionally, it may be determined whether the image of the object of interest is likely to be distorted by metal artifacts caused by the metal object. For example, although a metal object is in close proximity to the object of interest, it may be determined that the size of the metal object relative to the object of interest renders it unlikely that the metal object will have a significant negative effect on the image of the object of interest (e.g., if the metal object is much smaller than the object of interest). If a potential target object is in the vicinity of a metal object, such that the image of the object is likely to be distorted by metal artifacts, a metal artifact correction is performed on the slice containing the metal artifacts, according to one aspect (feedforward mode) of the invention described herein.

If it is determined in step 33 that a potential target object is in the vicinity of a metal object, information fed forward from the prescanner device is used to predict the type and shape of metal responsible for the metal artifacts in step 35. In particular, the mass information and effective atomic number information from Table A are used to identify the metal type and perform a metal artifact correction specific to the type and shape of the metal. The metal artifact correction algorithm is described in detail below in connection with FIG. 7.

In step 37, the scanned CT images are analyzed. According to one embodiment, the density, area, and three-dimensional coordinates are determined for each target object, for example using image processing algorithms (e.g., region growing). The area of each target object is specified by a range of two-dimensional (e.g., $x_1$–$x_2$, $y_1$–$y_2$ in FIG. 6) coordinates that delimit a region where the density of each pixel falls within a certain range. Further, a confidence level is determined for the density and area values associated with each pixel. Each confidence level represents a probability that the density or area data corresponding to that pixel is correct.

In step 39, a table (Table B) is generated containing the density, area, and three-dimensional coordinates for each target object, and a confidence level for each characteristic of each target object. Table B may be stored electronically by a memory (not shown) coupled to a processor and may, along with or separate from the processor, be either internal or external to CT scanner device 3. The three-dimensional coordinates for each target object are transmitted ("fed back") to prescanner device 1 in step 41. According to one aspect (feedback mode) of the invention, this information from Table B may be used to augment Table A. The processor, coupled to the memory that stores Table A, considers the fedback information and the information in Table A in determining whether to update any of the information in Table A.

Since prescanner device 1 images the item from only one view, the prescanner device may not be able to discern whether an identified object is a single object or a plurality of objects, as objects that overlap when imaged from a particular perspective may appear as a single merged object. If the prescanner device cannot differentiate a plurality of overlapping objects, it may determine a mass value for an object that is actually the mass values of two or more objects combined. The three-dimensional coordinate information provided in Table B can be used to differentiate objects, and thereby correct erroneous effective atomic number values and mass values of Table A. If the mass of an object changes, the object may no longer be of interest or, conversely, may become interesting. For example, if an original mass determination is based on two merged non-target objects, the mass value will be erroneously high, and may fall within the range corresponding to a target object. When the two merged objects are differentiated and their masses are determined separately, the individual objects may no longer be of interest if the mass value falls below a minimum mass associated with potential target objects.

In sum, the information fedback from Table B by the CT scanner device allows for more accurate determinations of the effective atomic number and mass of each object, as listed in Table A, by the prescanner device. Hence, superior detection by the prescanner device and a lower false alarm rate may be achieved by feeding back information from the CT scanner device to the prescanner device. It should be appreciated that multiple feedforward/feedbackwards loops are possible, whereby information generated by the prescanner device 1 and CT scanner device 3 is alternately transmitted between the two devices. It should be appreciated that the information from Table B need not be transmitted to the prescanner device. Rather, the CT scanner device or an external computer may implement an algorithm, similar to that which may be implemented by the prescanner, to augment Table A based on the Table B information.

In step 27, a decision is made based on the information in Tables A and B as to an appropriate course of action. As discussed above, possible actions include returning the baggage to the passenger, searching the baggage by hand, or calling the bomb squad. An algorithm may be used to synthesize the information of the two tables to determine an appropriate action. For each potential target object, the algorithm may consider the effective atomic number, density, and associated confidence levels for each, as well as the thickness of the potential target object and the proximity of the potential target object to metal. Based on the information, a likelihood is determined that an identified object is a target object. The likelihood is derived from a histogram representing, for example, the probability that an object having a given effective atomic number, density, thickness, mass, and proximity to metal is a target object, and may be represented as a probability that the object is a target object or as an absolute indication that the object is/is not a target object. It should be appreciated that any of the automated decisions or actions described above may alternatively be performed by a human operator.

FIG. 7 illustrates by flow diagram a method for obtaining a CT image and predicting and correcting metal artifacts of the CT image, most steps of which, as illustrated, correspond to step 35 described above in connection with FIG. 4. Like FIG. 4, the flow diagram of FIG. 7 shows both information (i.e., data) flow (in phantom lines) and process flow (in solid lines).

In step 43, a CT image is generated. Uncorrected CT images may contain metal artifacts when a scan is performed within a certain proximity to metal, which may result in inaccuracies. For example, beam hardening artifacts cause inaccuracies in the estimation of attenuation coefficients for pixels associated with x-rays that traverse highly attenuating structures. Streaky shadows or star patterns of streaks may result near high density objects in regions of pixels where essentially no attenuation information exists. Scatter artifacts may result from the dispersion of X-ray photons by the atoms within the item, and may cause noise in the CT image.

In step 45, the image is clipped so that the image contains only the metal that accounts for the artifacts of the image. The region to be clipped is identified by considering the effective atomic number information of Table A. Each pixel in the image of the metal will have an effective atomic number that falls within a range corresponding to the effective atomic number of the metal. The clipped image contains only the image of the metal, and does not contain the object of interest or artifacts.

The use of dual energy levels in the prescanner device makes it possible to determine the characteristics of the metal in the image. In step 47, the type of metal and thickness of the metal in the image are identified based on the information in Table A. In particular, the effective atomic number information of Table A is used to identify the type of metal and the mass information of Table A is used to determine the thickness of the metal.

A sinogram of the clipped image is generated in step 49. As discussed above, a single sinogram contains the information about a particular slice from all angles, with the information from each angle in its own row.

In step 51, a table (Table C) is generated that contains beam hardening, noise, and scatter correction parameters. The correction parameters are determined according to algorithms well-known in the art for compensating for beam hardening, noise, and scatter, based on the type and thickness of metal responsible for the artifacts.

In step 53, artifacts are introduced into the sinogram of the clipped image using the table (Table C) generated in step 51. In particular, the sinogram is corrupted using beam hardening and scatter effects based on the shape and type of the metal responsible for the artifacts, determined in step 47. The sinogram of the image of the metal and artifacts is reconstructed in step 55.

In step 57, the reconstructed artifact image generated in step 55 is subtracted from the sum of the original CT image generated in step 43 and the clipped image generated in step 45. The result of the image subtraction is a metal artifact corrected image 59. The image will result in a more accurate determination as to whether the object of interest represents a target object.

In an embodiment, the artifact image may also used as a map for determining whether the CT values read in the image are accurate.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and equivalents thereto.

The invention claimed is:

1. A method for analyzing an object comprising:
   prescanning the object using a multiple energy X-ray device to determine prescan information;
   transmitting the prescan information to a processor coupled to a computed tomography device;
   performing a computed tomography scan of at least a portion of the object based on the prescan information, wherein the computed tomography scan generates computed tomography scan data and is performed using the computed tomography device; and
   performing a metal artifact correction on the computed tomography scan data, wherein the prescan information is used to perform the metal artifact correction on the computed tomography scan data.

2. The method of claim 1, wherein the processor is located within the computed tomography device.

3. The method of claim 1, wherein prescanning comprises prescanning the object using a second computed tomography device.

4. A method for analyzing an object comprising:
   prescanning the object using a multiple energy X-ray device to determine information indicative of effective atomic number characteristics of the object;
   transmitting, to another device that is separate from and coupled to the multiple energy X-ray device, a transmission that is based at least partially on the information; and
   using the information received at the device to process scan data generated by a computed tomography device.

5. The method of claim 4, wherein the another device is a processor coupled to the computed tomography device, and wherein at least a portion of the multiple energy X-ray device is not common to the computed tomography device.

6. The method of claim 4, further comprising:
   using the information to select an area of interest of the object based upon the information; and
   conducting a scan of the area of interest of the object with the computed tomography device to generate the scan data.

7. The method of claim 4, wherein using the information received at the device to process scan data comprises using the information to apply a metal artifact correction algorithm to the scan data.

8. The method of claim 4, wherein the transmission comprises the information.

9. The method of claim 4, wherein using the information received at the device to process scan data comprises using the information to determine a type of a metal positioned to create a metal artifact in the scan data.

10. The method of claim 4, wherein using the information received at the device to process scan data comprises using the information to determine a shape of a metal positioned to create a metal artifact in the scan data.

11. The method of claim 4, wherein using the information received at the device to process scan data comprises using the information to make a decision relating to threat detection.

12. The method of claim 4, wherein the multiple energy x-ray device comprises a processor that is separate from the device.

* * * * *